US00PP15971P2

(12) United States Plant Patent
van Noort

(10) Patent No.: US PP15,971 P2
(45) Date of Patent: Sep. 20, 2005

(54) ***TRADESCANTIA* PLANT NAMED 'PINK CHABLIS'**

(50) Latin Name: *Tradescantia×andersoniana*
Varietal Denomination: Pink Chablis

(75) Inventor: Marcus Wilhelmus Gerardus van Noort, Warmond (NL)

(73) Assignee: Witteman & Company, Hillegom (NL)

( * ) Notice: Subject to any disclaimer, the term of this patent is extended or adjusted under 35 U.S.C. 154(b) by 64 days.

(21) Appl. No.: 10/878,424

(22) Filed: Jun. 28, 2004

(51) Int. Cl.[7] ..... A01H 5/00
(52) U.S. Cl. ..... Plt./263

(58) Field of Search ..... Plt./263

(56) References Cited

PUBLICATIONS

UPOV hit on 'Pink Chablis', UPOV–Rom Apr. 15, 2003.*

* cited by examiner

*Primary Examiner*—Anne Marie Grunberg
(74) *Attorney, Agent, or Firm*—C. A. Whealy

(57) ABSTRACT

A new and distinct cultivar of *Tradescantia* plant named 'Pink Chablis', characterized by its upright and outwardly spreading plant habit; freely flowering habit; and light red purple and white bi-colored petals with ruffled margins.

1 Drawing Sheet

Botanical classification/cultivar designation: *Tradescantia×andersoniana* cultivar Pink Chablis.

BACKGROUND OF THE INVENTION

The present Invention relates to a new and distinct cultivar of *Tradescantia* plant, botanically known as *Tradescantia×andersoniana,* and hereinafter referred to by the name 'Pink Chablis'.

The new *Tradescantia* originated from a cross-pollination of two unknown selections of *Tradescantia×andersoniana,* not patented. The new *Tradescantia* was discovered and selected as a single flowering plant by the Inventor in a controlled environment in Warmond, The Netherlands in 1999 from the resultant progeny of the cross-pollination.

Asexual reproduction of the new cultivar by cuttings at Warmond, The Netherlands since 2000, has shown that the unique features of this new *Tradescantia* are stable and reproduced true to type in successive generations.

SUMMARY OF THE INVENTION

Plants of the cultivar Pink Chablis have not been observed under all possible environmental conditions. The phenotype may vary somewhat with variations in environment such as temperature and light intensity without, however, any variance in genotype.

The following traits have been repeatedly observed and are determined to be the unique characteristics of 'Pink Chablis'. These characteristics in combination distinguish 'Pink Chablis' as a new and distinct *Tradescantia* cultivar:

1. Upright and outwardly spreading plant habit.
2. Freely flowering habit.
3. Light red purple and white bi-colored petals with ruffled margins.

Plants of the new *Tradescantia* can be compared to plants of the *Tradescantia* cultivar Sweet Kate, not patented. In side-by-side comparisons conducted in Warmond, The Netherlands, plants of the new Tradescantia differed from plants of the cultivar Sweet Kate in the following characteristics:

1. Plants of the new *Tradescantia* were slightly shorter than plants of the cultivar Sweet Kate.
2. Plants of the new *Tradescantia* had darker green-colored foliage than plants of the cultivar Sweet Kate.
3. Plants of the new *Tradescantia* and the cultivar Sweet Kate differed in flower color as plants of the cultivar Sweet Kate had blue-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Tradescantia.*

The photograph at the top of the sheet comprises a side perspective view of a typical plant of 'Pink Chablis' grown in a container.

The photograph at the center of the sheet is a close-up view of a typical flower of 'Pink Chablis'.

The photograph at the bottom of the sheet is a close-up view of the upper surface of a typical leaf of 'Pink Chablis'.

DETAILED BOTANICAL DESCRIPTION

Plants shown in the aforementioned photographs and used in the following description were grown under conditions which closely approximate commercial production conditions during the summer in an outdoor nursery in Warmond, The Netherlands. Plants were about two years old when the photographs and description were taken. During the production of the plants, day temperatures ranged from 18 to 32° C. and night temperatures ranged from 4 to 18° C. In the following description, color references are made to The Royal Horticultural Society Colour Chart, 2001 Edition, except where general terms of ordinary dictionary significance are used.

Botanical classification: *Tradescantia×andersoniana* cultivar Pink Chablis.

Parentage:

*Female, or seed, parent.*—Unknown selection of *Tradescantia×andersoniana,* not patented.

*Male, or pollen, parent.*—Unknown selection of *Tradescantia×andersoniana,* not patented.

Propagation:

*Type.*—By cuttings.

*Time to initiate roots.*—About 15 days at 14° C.

*Time to produce a rooted young plant.*—About 40 days at 20° C.

*Root description.*—Thick, fleshy.

Plant description:

*Form.*—Herbaceous perennial. Upright and outwardly spreading plant habit; inverted triangle. Flowering stems and leaves arise from the roots; moderately vigorous growth habit. About 18 flowering stems per plant.

*Growth rate.*—About 20 weeks are required to produce fully-grown flowering plants.

*Plant height.*—About 30 cm.

*Plant width.*—About 61 cm.

*Stem description.*—Length: About 30 cm. Diameter: About 6 mm. Texture: Smooth, glabrous. Color: 143A to 143B.

*Foliage description.*—Arrangement: Alternate, simple; sessile. Length: About 18.9 cm. Width: About 1.8 cm. Shape: Linear. Apex: Acute. Base: Sheathed. Margin: Entire. Texture, upper and lower surfaces: Mostly glabrous; sparse pubescence at margins. Venation pattern: Parallel. Color: Developing and fully expanded foliage, upper surface: Between 143A and 144A; venation, same as lamina. Developing and fully expanded foliage, lower surface: 138B; venation, same as lamina.

Flower description:

*Flower arrangement and shape.*—Single flowers arranged in cincinni subtended by linear to laceolate-shaped bracts. Freely flowering habit; about 40 flowers and flower buds per inflorescence. Flowers face upright to outward.

*Natural flowering season.*—Continuous flowering from mid-June to late August in The Netherlands.

*Flower longevity on the plant.*—Individual flowers last about five weeks on the plant. Flowers not persistent.

*Fragrance.*—None detected.

*Flower buds.*—Length: About 1 cm. Diameter: About 6 mm. Shape: Ovate. Color: 144B to 144C.

*Flowers.*—Diameter: About 2.6 cm. Depth (height): About 1.2 cm.

*Petals.*—Quantity per flower: Three. Length: About 1.4 cm. Width: About 1.6 cm. Shape: Roughly flabellate. Apex: Obtuse. Margin: Entire; undulate. Texture, upper and lower surfaces: Smooth; glabrous. Color: When opening, upper surface: 72C. When opening, lower surface: 72D. Fully opened, upper surface: 73A; towards the margins, 73D to close to 155D. Color becoming closer to 73D with development. Fully opened, lower surface: 73B; towards the margins, 73D to close to 155D.

*Sepals.*—Quantity per flower: Three. Length: About 1.1 cm. Width: About 4 mm. Shape: Ovate. Apex: Acute. Margin: Entire. Texture, upper and lower surfaces: Smooth, glabrous. Color, upper and lower surfaces: 144B to 144C.

*Pedicels.*—Length: About 1.6 cm. Diameter: About 1 mm. Angle: About 45° from vertical. Strength: Strong. Color: 177A.

*Reproductive organs.*—Stamens: Quantity per flower: Six. Anther attachment: Basifixed. Anther shape: Orbicular; flattened. Anther length: About 1 mm. Anther color: 14A to 14B. Filament length: About 1.1 cm. Filament color: 72D to 73A. Filament hairs: About 30 hair-like structures develop at the base of each filament; about 4 mm in length; 72D to 73A in color. Pollen amount: Moderate. Pollen color: 14B. Pistils: Quantity per flower: One. Pistil length: About 8 mm. Stigma shape: Club-shaped; flattened. Stigma color: 157D. Style length: About 7.5 mm. Style color: 72D to 73A. Ovary color: N145B.

*Seed/fruit.*—Seed and fruit development have not been observed.

Disease/pest resistance: Plants of the new *Tradescantia* have not been noted to be resistant to pathogens and pests common to *Tradescantia.*

Temperature tolerance: Plants of the new *Tradescantia* have been observed to tolerate temperatures from −10 to 35° C.

It is claimed:

1. A new and distinct cultivar of *Tradescantia* plant named 'Pink Chablis', as illustrated and described.

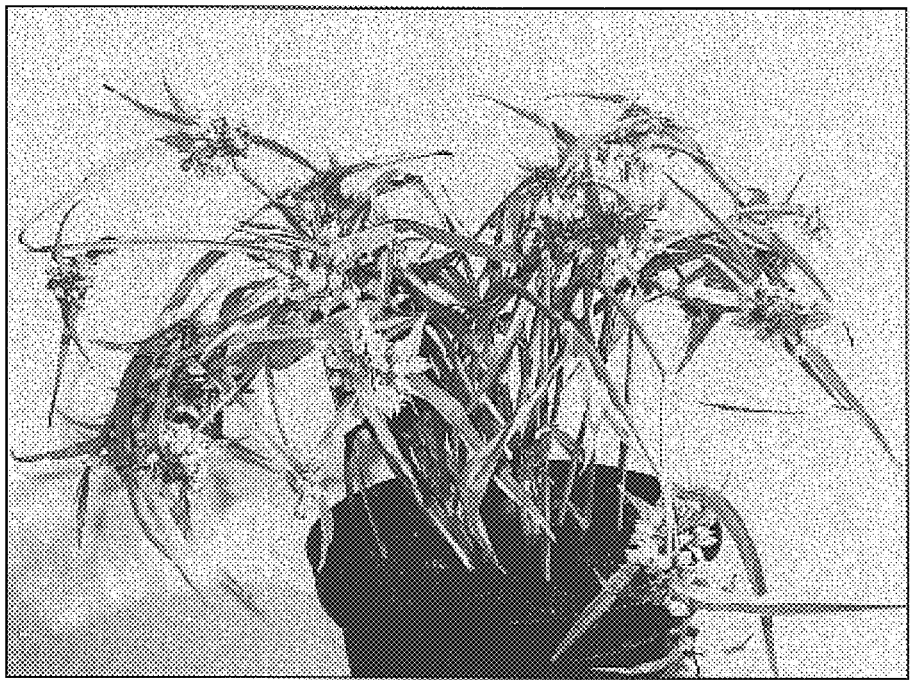
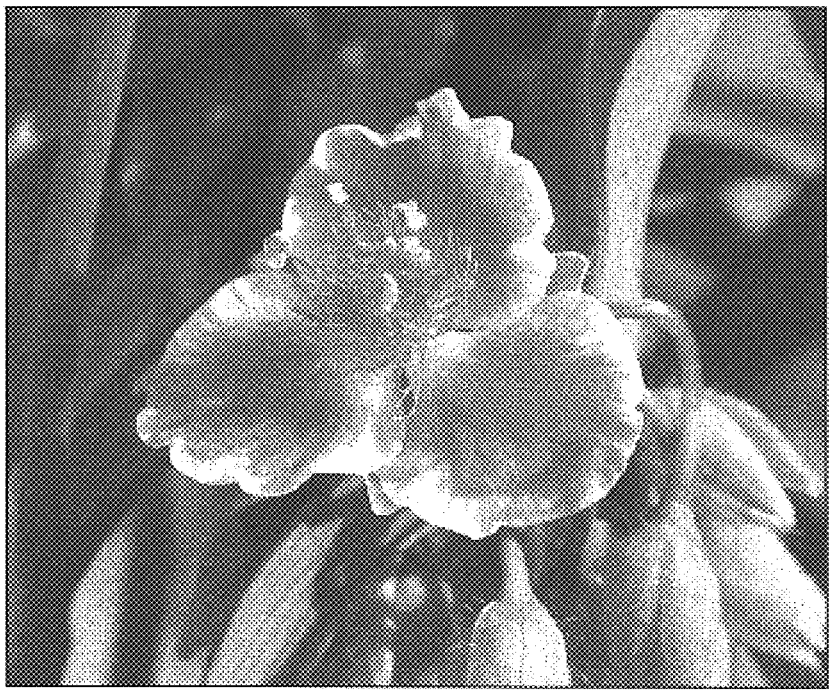
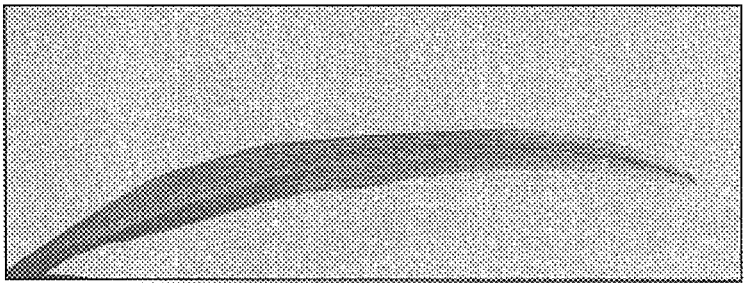

* * * * *